United States Patent [19]

Williams

[11] Patent Number: 6,093,423
[45] Date of Patent: Jul. 25, 2000

[54] REDUCED ABSORPTION OF FATTY ACIDS

[75] Inventor: Alun Roy Williams, Stockport, United Kingdom

[73] Assignee: Kappa Pharmaceuticals Limited, United Kingdom

[21] Appl. No.: 08/845,573

[22] Filed: Apr. 25, 1997

Related U.S. Application Data

[63] Continuation of application No. 08/600,950, filed as application No. PCT/GB94/01857, Aug. 24, 1994, abandoned.

[30] Foreign Application Priority Data

Aug. 24, 1993 [GB] United Kingdom .................. 9317568
Mar. 1, 1994 [GB] United Kingdom .................. 9403906

[51] Int. Cl.$^7$ ........................ A61K 33/06; A61K 33/00; A61K 33/04; A61K 33/24
[52] U.S. Cl. ........................ 424/696; 424/617; 424/661; 424/667; 424/673; 424/677; 424/682; 424/697; 424/703; 424/718; 424/722
[58] Field of Search ..................... 424/677, 682, 424/696, 697, 617, 661, 667, 673, 703, 718, 722

[56] References Cited

U.S. PATENT DOCUMENTS

| 4,325,975 | 4/1982 | Lindon et al. | ........................... | 426/66 |
| 4,447,417 | 5/1984 | Spickett et al. | ........................ | 424/686 |
| 4,780,307 | 10/1988 | Ben-Sasson | ............................. | 423/626 |

FOREIGN PATENT DOCUMENTS

| 150792 | 8/1985 | European Pat. Off. . |
| 166440 | 1/1986 | European Pat. Off. . |
| 2266217 | 10/1993 | United Kingdom . |
| 9413304 | 6/1994 | WIPO . |

OTHER PUBLICATIONS

Lapre, John A. et al., "The Antiproliferative Effect of Dietary Calcium on Colonic Epithelium . . ." Cancer Research, vol. 53(4), Feb. 15, 1993, pp. 784–789.
Chemical Abstracts 63:75396 (1965).

*Primary Examiner*—John Pak
*Attorney, Agent, or Firm*—Renner, Otto, Boisselle & Sklar

[57] ABSTRACT

A chemical agent for use in binding to and insolubilizing the solubilized products of fat digestion in order to prevent absorption of fat from the diet.

4 Claims, No Drawings

REDUCED ABSORPTION OF FATTY ACIDS

This is a continuation of application Ser. No. 08/600,950 filed on Feb. 21, 1996 now abandoned, which is a 371 of "PCT/GB94/01857, filed on Aug. 24, 1994.

This invention concerns the administration of one or more substances which reduce the proportion of fatty acid molecules which are absorbed from the gut contents following the digestion of a fatty meal.

People who wish to reduce their body weight usually go on a low calorie diet, i.e., they reduce their calorific intake. Since fats or lipids are a highly concentrated source of energy and, therefore, calories, most diets aim to reduce the amount of fat consumed.

However, low fat diets are often uninteresting and unappetising and quite often a dieter will relapse from their diet and consume a high fat snack or meal.

The present invention provides a substance which may be taken after the consumption of a fatty snack or meal which will reduce the amount of fat absorbed from the fatty snack or meal and thus may provide relief to people on low fat diets when they have a temporary relapse.

According to the present invention there is provided the use of a chemical agent selected from any one of the group of the ions of a group II metal, the ions of a group III metal, or a salt thereof, in the manufacture of a medicament for the prevention of absorption of fat from the diet, wherein the chemical agent binds to an insolubilises the products of fat digestion. This occurs in the environment of the small intestine so that the fat reaches the rectum and is excreted therefrom, thus preventing is absorption.

Dietary triacylglycerol is the major source of dietary fat for Western man. The digestion of triacylglycerol occurs mainly in the small intestine into which flow both bile and the secretions of the pancreas. Pancreatic lipase breaks down triacylglycerol into monoacylglycerol and fatty acids which, together with the bile salts, form soluble micelles. The fatty acids are in the form of sodium or potassium salts within the micelles. The micelles diffuse across the 'unstirred water layer' of the small intestine and come into contact with the microvillus membrane of the absorptive cells. Here the micelles dissociate to produce locally high concentrations of monoacylglycerol and fatty acids which are absorbed while the bile salts remain in the lumen (to be absorbed in the lower regions of the intestine).

The chemical agent of the present invention acts by dissociating and/or preventing micellar formation by displacing sodium or potassium ions from the micellar complexes.

Examples of such chemical agents would be the ions of group II metals such as calcium and magnesium and of group III metals such as aluminium.

These metals may be in the form of a salt, for example sulphate, and are taken in doses which are non-toxic.

One or more of the chemical agents of the present invention may be taken to prevent absorption of fat from the diet and thus effectively reduce the calorific value of a given meal.

The chemical agents may be active in the form in which they are administered, or they may become active as a result of the chemical environment existing within the gastrointestinal system. By 'active' is meant that the solubility product of chemical agent is greater than that of the ion plus free fatty acid so that the free fatty acid forms a salt with the ion of the chemical agent. Any dietary ingredient which has a lower solubility product than the fatty acid salt so formed will displace the fatty acid from the ion and thus release free fatty acids which may become available for absorption. Thus care should be taken to avoid such dietary ingredients, for example, oxalates.

The chemical agent may be taken immediately after consuming a fatty meal or within 2 hours of consuming a fatty meal.

The invention will be further apparent from the following preliminary experimental data.

PRELIMINARY EXPERIMENTAL DATA

Shortly after the consumption of a high fat meal, for example, fish and chips, a dose of magnesium sulphate or calcium sulphate was taken and the faeces collected for chemical analysis of its fat content using the Van de Kamer technique as follows;

1. The faecal specimen was weighed before being blended with water to uniform consistency.
2. A weighed portion of the blended sample was heated at 120° C. for 4–5 h until completely dry and re-weighed.
3. A second sample of the homogenate was transfered to a flask and weighed.
4. 10 ml of 6.2 molar KOH was added to the homogenate and mixed well. 40 ml of ethanol-isoamyl alcohol was added and the mixture boiled in a reflux system for at least 30 minutes before being cooled to room temperature.
5. 17 ml of 8.2 molar HCl was added and mixed thoroughly and the mixture cooled again.
6. 50 ml of petroleum ether was added and the sample shaken vigorously for one minute, the liquid phase was then allowed to settle.
7. 25 ml of the petroleum ether solution was transfered to a beaker and heated until the petroleum ether had evaporated. The residue containing fatty acids and sterols was weighed.
8. Alternatively, the petroleum ether of a 25 ml sample was boiled off before 10 ml redistilled ethanol was added and boiled gently for a few seconds to expel $CO_2$. 250 $\mu$m of thymol blue was added and the fatty acids in the sample titrated with 0.1 molar sodium hydroxide using a stream of nitrogen for mixing during the titration.

Calculations of the total fatty acid and lipid content of the total wet weight of faeces were carried out using the equations in Van de Kamer (Standard methods of Clinical Chemistry, Ed D. Seligson, Academic Press, New York, 1958 Vol II, pp34–39).

RESULTS

TABLE 1

| $CaSO_4$ ingested | Total FFA- | Total lipid |
|---|---|---|
| 1.0 g | 4.18 g | 6.49 g |
| 1.0 g | — | 5.00 g |
| 10.0 g | 8.85 g | 11.60 g |
| 6.0 g | 5.63 g | 5.12 g |
| 6.0 g | 7.87 g | 10.53 g |
| 6.0 g | 3.10 g | 6.47 g |
| CONTROL | 2.00 g | 3.90 g |

*FFA = Free Fatty Acid

CONCLUSION

Calcium sulphate taken within 2 hours of a fatty meal increased the faecal fat content significantly, thus preventing that fat from being absorbed from the small intestine thereby reducing the calorific value of that meal.

FURTHER EXPERIMENTAL DATA

A controlled study was performed to investigate the effects of calcium sulphate upon the absorption of dietary fat following consumption of medium and high fat meals.

The study comprised two treatment periods of four days separated by a 10 day washout period, making a total of four weeks. The participants in the study were a group of twelve healthy volunteers—10 male, 2 female—aged between 22 and 37. The volunteers were allocated at random to one of two groups and were given a treatment thirty minutes after each of three daily meals. The first group received doses of 5 g of calcium sulphate in the first treatment period and the second group received an inert placebo of 5 g of maize starch. After the first washout period the volunteers were crossed over to receive the alternate treatment in the second period. The volunteers did not know which preparation they were receiving in each treatment period.

The volunteers remained at the clinic throughout the treatment period and ate standard meals of known fat content. All the faecal samples produced during the treatment periods were collected and the quantity of lipid and fatty acids measured.

RESULTS

The results of this study were analysed using a standard Hills and Armitage statistical technique (Hills, M and Armitage, P [1979]. The two period cross-over clinical trial. British Journal of Clinical Pharmacology Vol. 8, pp 7–20). A statistically significant difference in the levels of faecal lipds and fatty acids was taken as the probability of the difference occuring by chance alone being less than 0.05 (5%).

Seven of the twelve volunteers showed a marked increase in levels of fat excretion during treatment with calcium sulphate, the mean increase being 42% more lipids and 37% more fatty acids. Results of the study are summarised in Table 2.

TABLE 2

| Total Output over Treatment Period | Treatment with | | |
|---|---|---|---|
| | Calcium Sulphate | Placebo | p-Value |
| Faecel lipids (g) | 345 | 260 | 0.031 |
| Faecel fatty acids (g) | 207 | 161 | 0.056 |

These results show that significantly more lipids were excreted in the volunteers' faeces when they were receiving calcium sulphate than when they were receiving the placebo. More fatty acids were also excreted during treatment with calcium sulphate, although with a p-value of 0.056 the result is not statistically significant. However, it does show that a statistical trend exists.

During the study, no serious adverse effects were recorded and no clinically significant laboratory changes were detected including the fat soluble vitamins A, D and E.

A normal upper limit for total fat content of the faeces is around 5.5 g. Fat above this level is considered clinically as steatorrhoea. The main causes of steatorrhoea are billiary obstruction, in which the bile duct is blocked resulting in reduce bile salts in the lumen, liver disease resulting in reduced production of bile and pancreatic disease where pancreatic lipase is reduced in the lumen.

It is thus important not to confuse the steatorrhoea caused by the chemical agents of the present invention with the above mentioned clinical conditions.

It is not recommended that the chemical agents of the present invention be used on a long term basis. Steatorrhoea presents the bacteria of the large intestine with a source of food and energy not normally available to them. This causes bacterial overgrowth and all the problems associated with this, for example, increased flatulence. Therefore, to counteract the ill effects of any long term use of the chemical agents of the present invention it is advised that a person also take non-absorbable antibiotics to control the bacterial overgrowth in the large intestine.

It will be appreciated that it is not intended to limit the invention to the above example only, many variations, such as might readily occur to a person skilled in the art being possible, without departing from the scope thereof.

What is claimed is:

1. A method of reducing absorption of fat comprising the steps of consuming a fatty food and immediately thereafter or within two hours administering from 1 to 10 grams of calcium sulfate which binds to and insolubilizes products of fat digestion, wherein the calcium ions react with the products of fat digestion to form fatty acid salts.

2. The method of claim 1 wherein the calcium sulfate is taken in conjunction with another chemical agent or agents selected from (a) ions of a Group II metal, (b) ions of a Group III metal, (c) a salt thereof which binds to and insolubilizes products of fat digestion, or (d) non-absorbable antibiotics, wherein said another chemical agent or agents is other than calcium sulfate.

3. A method of reducing absorption of fat comprising the steps of consuming a fatty food at at least two meals per day and immediately thereafter or within two hours of each of the at least two meals administering from 1 to 10 grams of calcium sulfate which binds to and insolubilizes products of fat digestion, wherein the calcium ions react with the products of fat digestion to form fatty acid salts.

4. The method of claim 3 wherein the calcium sulfate is taken in conjunction with another chemical agent or agents selected from (a) ions of a Group II metal, (b) ions of a Group III metal, (c) a salt thereof which binds to and insolubilizes products of fat digestion, or (d) non-absorbable antibiotics, wherein said another chemical agent or agents is other than calcium sulfate.

* * * * *